US008748344B2

(12) United States Patent
Kisenwether et al.

(10) Patent No.: US 8,748,344 B2
(45) Date of Patent: Jun. 10, 2014

(54) AGRICULTURAL ADJUVANT COMPOSITIONS, PESTICIDE COMPOSITIONS, AND METHODS FOR USING SUCH COMPOSITIONS

(75) Inventors: Michael Kisenwether, Philadelphia, PA (US); Shanmuganandamurthy Krishnamurthy, Plainsboro, NJ (US); Rajesh Pazhianur, Belle Mead, NJ (US)

(73) Assignee: Rhodia Operations, Aubervilliers (FR)

( * ) Notice: Subject to any disclaimer, the term of this patent is extended or adjusted under 35 U.S.C. 154(b) by 503 days.

(21) Appl. No.: 12/804,115

(22) Filed: Jul. 14, 2010

(65) Prior Publication Data
US 2011/0015071 A1 Jan. 20, 2011

Related U.S. Application Data

(60) Provisional application No. 61/271,113, filed on Jul. 17, 2009, provisional application No. 61/270,811, filed on Jul. 14, 2009.

(51) Int. Cl.
| | | |
|---|---|---|
| A01N 63/00 | (2006.01) | |
| A01N 57/00 | (2006.01) | |
| A01N 57/12 | (2006.01) | |
| A01N 25/04 | (2006.01) | |
| A01N 25/30 | (2006.01) | |
| A01N 37/10 | (2006.01) | |
| A01N 39/02 | (2006.01) | |

(52) U.S. Cl.
CPC ............... *A01N 63/00* (2013.01); *A01N 25/04* (2013.01); *A01N 25/30* (2013.01); *A01N 37/10* (2013.01); *A01N 39/02* (2013.01); *A01N 57/12* (2013.01)
USPC ........ 504/116.1; 504/127; 504/142; 504/145; 504/199; 504/364; 504/556; 514/25; 514/556; 514/777

(58) Field of Classification Search
CPC ....... A01N 2/504; A01N 25/30; A01N 37/10; A01N 39/02; A01N 57/12; A01N 63/00
See application file for complete search history.

(56) References Cited

U.S. PATENT DOCUMENTS

| | | |
|---|---|---|
| 3,225,074 A | 12/1965 | Cowen et al. |
| 3,527,593 A | 9/1970 | Bland et al. |
| 3,723,357 A | 3/1973 | Hansen |
| 3,882,051 A | 5/1975 | Hansen |
| 4,011,388 A | 3/1977 | Murphy et al. |
| 4,107,328 A | 8/1978 | Michaels |
| 4,117,107 A | 9/1978 | Shapiro |
| 4,122,159 A | 10/1978 | Madrange et al. |
| 4,137,191 A | 1/1979 | Lohr |
| 4,243,549 A | 1/1981 | Messenger et al. |
| 4,452,732 A | 6/1984 | Bolich, Jr. |
| 4,477,365 A | 10/1984 | Verboom et al. |
| 4,585,846 A | 4/1986 | Schulz et al. |
| 4,607,076 A | 8/1986 | Schulz et al. |
| 4,650,848 A | 3/1987 | Schulz et al. |
| 4,703,797 A | 11/1987 | Djabbarah |
| 4,708,998 A | 11/1987 | Schulz et al. |
| 4,742,135 A | 5/1988 | Schulz et al. |
| 4,788,247 A | 11/1988 | Schulz et al. |
| 4,822,847 A | 4/1989 | Schulz et al. |
| 4,831,092 A | 5/1989 | Bock et al. |
| 4,835,234 A | 5/1989 | Valint et al. |
| 4,882,405 A | 11/1989 | Schulz et al. |
| 4,996,045 A | 2/1991 | Leighton et al. |
| 5,153,289 A | 10/1992 | Schulz et al. |
| 5,164,120 A | 11/1992 | Borland et al. |

(Continued)

FOREIGN PATENT DOCUMENTS

| | | |
|---|---|---|
| AU | 646915 | 10/1992 |
| CA | 2554335 | 8/2005 |

(Continued)

OTHER PUBLICATIONS

Ullmann's Encyclopedia of Industrial Chemistry, 5$^{th}$ Ed., vol. A 10, Edited by Gerhartz et al., pp. 176-177, Wiley-VCH Verlag GmbH & Co. KGaA, Weinheim, Germany, May 5, 1994.
"Application Guide for Household & Industrial Markets"; McIntyre Group Ltd., Copyright 2002, (Jan. 2003), obtained online @ http://www.dewolfchem.com/pdf/Mcintyre_HI&I_Application_Guide.pdf, (downloaded Mar. 6, 2012).
Surfactants by Albright & Wilson (Australia Limited CAN 004 234 137)—5 pp.
Basheva et al.; *Role of Betaine as Foam Booster in the Presence of Silicone Oil Drops*; Langmuir 2000, 16, 1000-1013; Received Jun. 16, 1999; 2000 American Chemical Society Published on Web Dec. 8, 1999.

*Primary Examiner* — Neil Levy

(57) ABSTRACT

An adjuvant composition contains an adjuvant composition, comprising, based on 100 parts by weight of the composition: (a) from about 10 to 100 parts by weight of a combined of one or more betaine surfactants and one or more glycoside surfactants, comprising, based on 100 parts by weight of the combined amount: (i) from greater than 0 to less than 100 parts by weight of the one or more betaine surfactants, and (ii) from greater than 0 to less than 100 parts by weight of one or more glycoside surfactants, and (b) from 0 to about 90 parts by weight water A pesticide composition contains based on 100 parts by weight of the composition: (a) from greater than 0 parts by weight to about 20 parts by weight of a combined amount of one or more betaine surfactants and one or more glycoside surfactants, comprising, based on 100 parts by weight of the combined amount: (i) from greater than 0 to less than 100 parts by weight of the one or more betaine surfactants, and (ii) from greater than 0 to less than 100 parts by weight of one or more glycoside surfactants, and (b) from 0 to about 90 parts by weight water, and (c) an effective amount of one or more pesticides. A method for controlling the growth of a target plant includes applying the pesticide composition to the target plant.

5 Claims, No Drawings

(56) References Cited

U.S. PATENT DOCUMENTS

| | | | |
|---|---|---|---|
| 5,180,414 A | 1/1993 | Darchy et al. |
| 5,258,358 A | 11/1993 | Kocur et al. |
| 5,292,942 A | 3/1994 | Aigner et al. |
| 5,338,793 A | 8/1994 | Loftin |
| 5,341,932 A | 8/1994 | Chen et al. |
| 5,354,906 A | 10/1994 | Weitmeyer et al. |
| 5,385,206 A | 1/1995 | Thomas |
| 5,439,317 A | 8/1995 | Bishop et al. |
| 5,464,806 A | 11/1995 | Kassebaum et al. |
| 5,551,516 A | 9/1996 | Norman et al. |
| 5,580,856 A | 12/1996 | Prestrelski et al. |
| 5,612,285 A | 3/1997 | Arnold |
| 5,686,400 A | 11/1997 | Urfer et al. |
| 5,700,760 A | 12/1997 | Magin et al. |
| 5,703,016 A | 12/1997 | Magin et al. |
| 5,747,416 A | 5/1998 | McArdle et al. |
| 5,863,863 A | 1/1999 | Hasebe et al. |
| 5,874,394 A | 2/1999 | Thomas et al. |
| 5,877,143 A | 3/1999 | Abbas et al. |
| 5,888,934 A | 3/1999 | Townson et al. |
| 5,897,699 A | 4/1999 | Chatterjl et al. |
| 5,912,209 A | 6/1999 | Kassebaum |
| 5,985,798 A | 11/1999 | Crudden |
| 5,998,332 A | 12/1999 | Sato et al. |
| 6,030,928 A | 2/2000 | Stahl et al. |
| 6,036,638 A | 3/2000 | Nwawka |
| 6,127,318 A | 10/2000 | Sato et al. |
| 6,165,939 A | 12/2000 | Agbaje et al. |
| 6,210,476 B1 | 4/2001 | Chatterjl et al. |
| 6,284,854 B1 | 9/2001 | Bowers et al. |
| 6,288,010 B1 | 9/2001 | Rose et al. |
| 6,302,209 B1 | 10/2001 | Thompson et al. |
| 6,329,322 B1 | 12/2001 | Reierson |
| 6,346,588 B1 | 2/2002 | Fench et al. |
| 6,369,122 B1 | 4/2002 | Subramanyam |
| 6,376,566 B1 | 4/2002 | Bergeron et al. |
| 6,407,042 B1 | 6/2002 | Ward et al. |
| 6,417,268 B1 | 7/2002 | Zhang et al. |
| 6,432,878 B1 | 8/2002 | Brigance |
| 6,432,884 B1 | 8/2002 | Lachut |
| 6,451,731 B1 * | 9/2002 | Agbaje et al. ............ 504/118 |
| 6,500,784 B1 | 12/2002 | Mille |
| 6,566,408 B1 | 5/2003 | Cotrell et al. |
| 6,642,178 B2 | 11/2003 | Woznica et al. |
| 6,645,912 B1 | 11/2003 | Mille et al. |
| 6,645,914 B1 | 11/2003 | Woznica et al. |
| 6,653,257 B2 | 11/2003 | Mille |
| 6,770,268 B1 | 8/2004 | Hall et al. |
| 6,770,594 B2 | 8/2004 | Bickers et al. |
| 6,831,108 B2 | 12/2004 | Dahanayake et al. |
| 6,992,046 B2 | 1/2006 | Bramati et al. |
| 7,135,437 B2 | 11/2006 | Pallas et al. |
| 7,316,990 B2 * | 1/2008 | Tank et al. ............ 504/206 |
| 8,236,730 B2 | 8/2012 | Bramati et al. |
| 8,263,529 B2 | 9/2012 | Suzuki et al. |
| 8,383,137 B2 | 2/2013 | Modaressi et al. |
| 2002/0187917 A1 | 12/2002 | Lazarowitz |
| 2003/0118540 A1 | 6/2003 | Charlton et al. |
| 2003/0158042 A1 | 8/2003 | Bramati et al. |
| 2004/0097372 A1 | 5/2004 | Abraham et al. |
| 2004/0110644 A1 | 6/2004 | Halliday et al. |
| 2004/0121917 A1 | 6/2004 | Pakulski |
| 2004/0224846 A1 | 11/2004 | Bramati et al. |
| 2005/0003965 A1 | 1/2005 | Xiao et al. |
| 2005/0010009 A1 | 1/2005 | Schultz et al. |
| 2005/0020454 A1 | 1/2005 | Francini et al. |
| 2005/0130842 A1 | 6/2005 | Fleute-Schlachter |
| 2005/0170965 A1 | 8/2005 | Bramati et al. |
| 2006/0019830 A1 | 1/2006 | Xu et al. |
| 2006/0058193 A1 | 3/2006 | Bramati et al. |
| 2006/0060354 A1 | 3/2006 | Lewis et al. |
| 2007/0155628 A1 * | 7/2007 | Pazhianur et al. ......... 504/116.1 |
| 2007/0282075 A1 | 12/2007 | Koch et al. |
| 2008/0103047 A1 | 5/2008 | Gioia et al. |
| 2008/0312083 A1 | 12/2008 | Gioia et al. |
| 2009/0018018 A1 | 1/2009 | Gioia et al. |
| 2010/0069269 A1 | 3/2010 | Prat et al. |
| 2010/0093874 A1 | 4/2010 | Monin et al. |
| 2010/0140531 A1 | 6/2010 | Prat et al. |
| 2010/0279869 A1 | 11/2010 | Bramati et al. |
| 2011/0009269 A1 | 1/2011 | Gioia et al. |
| 2012/0040833 A1 | 2/2012 | Kisenwether et al. |
| 2012/0165195 A1 | 6/2012 | Iskandar et al. |

FOREIGN PATENT DOCUMENTS

| | | |
|---|---|---|
| EP | 0373851 A2 | 6/1990 |
| EP | 0274369 B1 | 9/1990 |
| EP | 0483095 A2 | 4/1992 |
| EP | 0370338 B1 | 5/1992 |
| EP | 0508022 A1 | 10/1992 |
| EP | 0573118 A2 | 12/1993 |
| EP | 0449159 B1 | 7/1995 |
| EP | 0810239 B1 | 9/2000 |
| JP | 10183176 | 7/1998 |
| JP | 11-349826 | 12/1999 |
| WO | 92/12637 | 8/1992 |
| WO | WO 92/14907 | 9/1992 |
| WO | WO 97/01281 | 1/1997 |
| WO | 97/06230 | 2/1997 |
| WO | WO 97/36489 | 10/1997 |
| WO | WO 98/14060 | 4/1998 |
| WO | WO 99/03895 | 1/1999 |
| WO | WO 99/15610 | 4/1999 |
| WO | WO 99/45780 | 9/1999 |
| WO | WO 99/62338 | 12/1999 |
| WO | WO 00/38523 | 7/2000 |
| WO | WO 00/67571 | 11/2000 |
| WO | WO 00/67573 | 11/2000 |
| WO | WO 01/08482 | 2/2001 |
| WO | WO 01/17358 | 3/2001 |
| WO | WO 01/26463 | 4/2001 |
| WO | WO 01/26469 | 4/2001 |
| WO | 01/89302 | 11/2001 |
| WO | WO 02/26036 | 4/2002 |
| WO | WO 03/013241 | 2/2003 |
| WO | WO 03/049813 | 6/2003 |
| WO | 2004/107862 | 12/2004 |
| WO | WO 2004/107861 | 12/2004 |
| WO | 2007/003112 | 1/2007 |

* cited by examiner

AGRICULTURAL ADJUVANT COMPOSITIONS, PESTICIDE COMPOSITIONS, AND METHODS FOR USING SUCH COMPOSITIONS

FIELD OF THE INVENTION

This invention relates to agricultural adjuvant compositions, pesticide compositions, and methods for using such compositions.

BACKGROUND OF THE INVENTION

Many agricultural pesticides, including insecticides, fungicides, herbicides, miticides, and plant growth regulators, are applied in the form of a liquid composition. In addition to the pesticide and a solvent, such liquid compositions typically include one or more adjuvant compounds intended to improve one or more properties of the liquid composition, such as for example, storage stability, ease of handling, pesticide efficacy against target organisms.

There is a continuing interest in pesticide compositions that exhibit improved properties.

SUMMARY OF THE INVENTION

In a first aspect, the present invention is directed to an adjuvant composition, comprising, based on 100 parts by weight of the composition:
(a) from about 10 to 100 parts by weight of a combined amount of one or more betaine surfactants and one or more glycoside surfactants, comprising, based on 100 parts by weight of the combined amount:
  (i) from greater than 0 to less than 100 parts by weight of the one or more betaine surfactants, and
  (ii) from greater than 0 to less than 100 parts by weight of one or more glycoside surfactants, and
(b) from 0 to about 90 parts by weight water.

In one embodiment, the adjuvant composition of the present invention comprises based on 100 parts by weight of the composition:
(a) from about 10 to 100 parts by weight of a combined amount of one or more betaine surfactants and one or more glycoside surfactants, comprising, based on 100 parts by weight of the combined amount:
  (i) from about 50 to less than 100 parts by weight of the one or more betaine surfactants, and
  (ii) from greater than 0 to about 50 parts by weight of one or more glycoside surfactants, and
(b) from 0 to about 90 parts by weight water.

In a second aspect, the present invention is directed to a pesticide composition, comprising, based on 100 parts by weight of the composition:
(a) from greater than 0 parts by weight to about 20 parts by weight of a combined amount of one or more betaine surfactants, and one or more glycoside surfactants, comprising, based on 100 parts by weight of the combined amount:
  (i) from greater than 0 to less than 100 parts by weight of the one or more betaine surfactants, and
  (ii) from greater than 0 to less than 100 parts by weight of one or more glycoside surfactants,
(b) water, and
c) one or more pesticides.

In one embodiment, the pesticide composition of the present invention comprises, based on 100 parts by weight of the composition:
(a) from greater than 0 parts by weight to about 20 parts by weight of a combined amount of one or more betaine surfactants, and one or more glycoside surfactants, comprising, based on 100 parts by weight of the combined amount:
  (i) from greater than 0 to less than 100 parts by weight of the one or more betaine surfactants, and
  (ii) from greater than 0 to less than 100 parts by weight of one or more glycoside surfactants,
(b) water, and
(c) one or more pesticides.

In a third aspect, the present invention is directed to a method for controlling the growth of a target plant, comprising applying the above described pesticide composition to the target plant.

DETAILED DESCRIPTION OF INVENTION AND PREFERRED EMBODIMENTS

As used herein, the term "alkyl" means a saturated straight chain or branched chain hydrocarbon radical, such as for example, methyl, ethyl, n-propyl, iso-propyl, n-butyl, sec-butyl, t-butyl, pentyl, andn-hexyl, As used herein, the term "alkoxyl" means an oxy group substituted with an alkyl group, such as, for example, methoxyl, ethyoxyl, propoxyl.

As used herein, the term "cycloalkyl" means a saturated cyclic hydrocarbon radical, such as, for example, cyclopentyl, cyclohexyl.

As used herein, the term "hydroxyalkyl" means a saturated straight chain or branched chain hydrocarbon radical substituted one or more carbon atoms with a hydroxyl group, such as for example, hydroxymethy, hydroxyethyl, hydroxypropyl.

As used herein, the term "alkenyl" means an unsaturated straight chain, branched chain, or cyclic hydrocarbon radical that contains one or more carbon-carbon double bonds, such as, for example, ethenyl, 1-propenyl, and 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "aralkyl" means an alkyl group substituted with one or more aryl groups, such as, for example, phenylmethyl, phenylethyl, and triphenylmethyl.

As used herein, the term "alkylamido" means amido radical, substituted with an alkyl group, such as dodecylamido, tetradecylamido.

As used herein, the term "alkylamidoalkyl" means an alkyl group substituted with an alkylamido group, such as dodecylamidoalkyl, tetradecylamidoalkyl.

As used herein, the terminology "$(C_n$-$C_m)$" in reference to an organic group, wherein n and m are each integers, indicates that the group may contain from n carbon atoms to m carbon atoms per group.

As used herein, the term "agronomically acceptable salts" refers to salts prepared from agronomically acceptable non-toxic bases or acids including inorganic or organic bases and inorganic or organic acids. Typical agronomically acceptable salts the compound referred to herein comprise an anion derived from the compound, for example, by deprotonation of a hydroxy or hydroxyalkyl substituent, and one or more positively charged counterions. Suitable positively charged counterions include inorganic cations and organic cations, such as for example, sodium cations, potassium cations, calcium cations, magnesium cations, isopropylamine cations, ammonium cations, and tetraalkylammonium cations.

References herein to saccharide compounds and moieties, such as, for example, glycosides, polyglycosides, and residues thereof, include, unless otherwise explicitly limited, all linear and cyclized forms of the saccharide compound or moiety, as well as isomers thereof.

As used herein, the terminology "effective amount" in reference to the relative amount of a pesticide in a pesticide composition means the relative amount of pesticide that is effective to control a target pest, for example, a target plant, fungus, bacterium, or insect, when the pesticide composition is applied at a given application rate.

As used herein, the terminology "an herbicidally effective amount" in reference to the relative amount of herbicide in an herbicidal composition means the relative amount that is effective to control growth of a target plant when the herbicidal composition is spray applied to the target plant at a given application rate.

In one embodiment the adjuvant composition of the present invention comprises, based on 100 parts by weight ("pbw") of the composition:
(a) from about 15 pbw, more typically about 20 pbw, and even more typically about 25 pbw, to about 80 pbw, more typically about 50 pbw, and even more typically about 40 pbw, of the combined amount of the one or more betaine surfactants and the one or more glycoside surfactants, and
(b) from about 20 pbw, more typically from about 50 pbw and even more typically from about 60 pbw, to about 85 pbw, more typically about 80 pbw, and even more typically about 75 pbw, water.

In one embodiment, the adjuvant composition of the present invention comprises, based on 100 pbw of the composition:
(a) from about 15 to about 80 pbw, more typically from about 20 to about 50 pbw, and even more typically from about 25 to about 40 pbw, of the combined amount of the one or more betaine surfactants and the one or more glycoside surfactants, and
(b) from about 20 to about 85 pbw, more typically from about 50 to about 80 pbw water and even more typically from about 60 to about 75 pbw water.

In one embodiment of the adjuvant composition of the present invention, the combined amount of the one or more glycoside surfactants and the one or more betaine surfactants comprises, based on 100 pbw of the combined amount:
(i) from about 60, more typically about 65 pbw, even more typically about 70 pbw, and still more typically about 75 pbw, to less than 100 pbw, more typically about 99 pbw, even more typically about 98 pbw, and still more typically about 97 pbw, of the one or more betaine surfactants, and
(i) from greater than 0, more typically about 1 pbw, even more typically about 2 pbw, and still more typically about 3 pbw, to about 40 pbw, more typically about 35 pbw, even more typically about 30 pbw, and still more typically about 25 pbw, of the one or more glycoside surfactants.

In one embodiment of the adjuvant composition of the present invention, the combined amount of the one or more glycoside surfactants and the one or more betaine surfactants comprises, based on 100 pbw of the combined amount:
(i) from about 60 to less than 100 pbw, more typically from about 65 to about 99 pbw, even more typically from about 70 to about 98 pbw, and still more typically from about 75 to about 97 pbw, of the one or more betaine surfactants, and
(i) from greater than 0 to about 40 pbw, more typically from about 1 to about 35 pbw, even more typically from about 2 to about 30 pbw, and still more typically from about 3 to about 25 pbw, of the one or more glycoside surfactants.

Betaine surfactants are known and include, for example, N-alkyl derivatives of glycine and N-alkyl derivatives of β-alanine, more typically N-alkyl derivatives of dimethyl glycine. In one embodiment, the betaine surfactant comprises one or more compounds according to formula (I):

wherein:
R is methylene or dimethylene,
$R^1$ and $R^2$ are each independently alkyl, alkenyl, alkoxyalkyl, hydroxyalkyl, hydroxy-terminated poly(oxyalkylene), or alkoxy-terminated poly(oxyalkylene), and
$R^3$ is a hydrophobic moiety.

In one embodiment, $R^1$ and $R^2$ are each independently $(C_1-C_6)$alkyl, $(C_1-C_6)$alkenyl, an alkoxyalkyl group having from 2 to 6 carbon atoms per group, hydroxy$(C_1-C_6)$alkyl, or $R^4$—$(OC_xH_{2x})_y$—, wherein $R^4$ is H or $(C_1-C_6)$alkyl, x is, independently for each —$(OC_xH_{2x})$— unit, 2 or 3, and y is an integer of from 1 to 20, more typically from 1 to 10. If $R^4$—$(OC_xH_{2x})_y$— is present and contains both —$(OC_xH_{2x})$— unit, 2 or 3, which X is 2, that is, oxyethylene units, and —$(OC_xH_{2x})$— units in which x is 3, that is, oxypropylene units, then the oxyethylene units and oxypropylene units may be arranged in random order or in blocks.

In one embodiment, $R^3$ is an alkyl, alkenyl, alkoxyalkyl, alkylaminoalkyl, alkylamidoalkyl, alkenylaminoalkyl, or alkenylamidoalkyl group, each typically having from 6 to 30 carbon atoms per group, wherein the alkyl moiety of the respective alkoxyalkyl, alkylaminoalkyl, and alkylamidoalkyl groups may optionally be substituted with one or more hydroxyl groups, and wherein the alkoxyalkyl group may optionally be linked to the nitrogen atom of structure (I) via a divalent oxyalkylene radical of from 1 to 6 oxy$(C_2-C_3)$ alkylene units.

In one embodiment:
R is methylene or dimethylene,
$R^1$ and $R^2$ are each independently $(C_1-C_3)$alkyl, and
$R^3$ is $(C_6-C_{30})$alkyl, alkoxyalkyl having from 6 to 30 carbon atoms per group, $(C_6-C_{24})$alkylamido$(C_1-C_6)$alkyl or $(C_6-C_{24})$alkenylamido$(C_1-C_6)$alkyl.

In one embodiment, R is methylene, $R^1$ and $R^2$ are each independently $(C_1-C_6)$alkyl, more typically methyl, and $R^3$ is $(C_6-C_{30})$alkyl, more typically $(C_8-C_{22})$alkyl, more typically $(C_8-C_{18})$alkyl, and still more typically, $(C_{12}-C_{16})$alkyl.

In one embodiment, R is methylene, $R^1$ and $R^2$ are each independently $(C_1-C_6)$alkyl, more typically methyl, and $R^3$ is alkylamidoalkyl, more typically $(C_6-C_{24})$alkylamido$(C_1-C_6)$ alkyl, and, even more typically, $(C_8-C_{20})$alkylam idopropyl.

Suitable betaines include, for example, decyl dimethyl betaine, undecyl dimethyl betaine, dodecyl dimethyl betaine, tridecyl dimethyl betaine, tetradecyl dimethyl betaine, coco dimethyl betaine, hexadecyl dimethyl betaine, heptadecyl dimethyl betaine, octadecyl dimethyl betaine, dodecylamidopropyl dimethyl betaine, cocoamidopropyl dimethyl betaine, oleylamidopropyl betaine, lauryl dihydroxypropyl glycinate, lauryl di(hydroxy-poly(ethoxy)) glycinate, β-alanine, cocodimethylbetaine, and mixtures thereof.

Glycoside surfactants are generally known compounds, which characteristically comprise a sugar moiety bound to a hydrophobic moiety. Suitable sugar moieties include monosaccharide moieties and polysaccharide moieties. Suitable hydrophobic moieties include hydrocarbyl moieties, more typically ($C_4$-$C_{30}$)hydrocarbyl moieties, even more typically ($C_4$-$C_{30}$)alkyl groups. In one embodiment, the glycoside surfactant component of the present invention is selected from alkylmonoglycoside surfactants, alkylpolyglycoside surfactants, and mixtures thereof.

In one embodiment, the glycoside surfactant comprises one or more compounds according to formula (II):

$$R^4O(R^5)_mR^6 \quad\quad (II)$$

wherein:
  $R^4$ is a hydrophobic moiety,
  each $R^5$ is independently a divalent monosaccharide radical,
  $R^6$ is a monovalent monosaccharide radical, and
  m is an integer of from 0 to about 10, more typically from 0 to 4, even more typically from 0 to 2.

In one embodiment, $R^4$ is hydrocarbyl, substituted hydrocarbyl. More typically, $R^4$ is a linear or branched saturated or unsaturated aliphatic group or an aromatic group, more typically, alkyl, cycloalkyl, aryl, or aralkyl, and even more typically, alkyl.

In one embodiment, $R^4$ contains from 4 to 30 carbon atoms, more typically from 6 to 24 carbon atoms and even more typically from 8 to 22 carbon atoms.

In one embodiment, $R^4$ is ($C_4$-$C_{22}$)alkyl. In another embodiment, $R^4$ is ($C_4$-$C_8$)alkyl. In another embodiment, $R^4$ is ($C_8$-$C_{14}$)alkyl. In another embodiment, $R^4$ is ($C_{14}$-$C_{22}$) alkyl.

As used herein in reference to a monosaccharide radical, the term "divalent" means that the radical is a linking group that links two other moieties via a respective single covalent bond between the divalent monosaccharide radical and each of the two other moieties and corresponds to a monosaccharide residue formed by, for example, conceptually removing two hydrogen atoms from a molecule of the monosaccharide. In one embodiment, each $R^5$ is a divalent radical selected from divalent pentose radicals and divalent hexose radicals. Suitable radicals include divalent radicals of aldopentoses, aldohexoses, ketopentoses, and ketohexoses, such as, for example, divalent radicals of ribose, arabinose, xylose, lyxose, allose, altrose, glucose, mannose, gulose, idose, galactose, talose, dihydroxyacetone, erthrulose, psicose, fructose, sorbose, and tagatose.

In one embodiment, each $R^5$ is independently a divalent radical of ribose, arabinose, xylose, lyxose, allose, altrose, glucose, mannose, gulose, idose, galactose, talose, dihydroxyacetone, erthrulose, psicose, fructose, sorbose, or tagatose.

In one embodiment, each $R^5$ is independently a divalent radical of glucose, arabinose, or xylose, more typically, glucose.

As used herein in reference to a monosaccharide radical, the term "monovalent" means that the radical is a an end group that caps one other moiety via a single covalent bond to the one other moiety and corresponds to a monosaccharide residue formed by, for example, conceptually removing one hydrogen atom from a molecule of the monosaccharide. In one embodiment, $R^6$ is a monovalent radical selected from monovalent pentose radicals and monovalent hexose radicals. Suitable pentoses and hexoses are those listed above in the description of $R^5$.

In one embodiment, $R^6$ is monovalent radical of ribose, arabinose, xylose, lyxose, allose, altrose, glucose, mannose, gulose, idose, galactose, talose, dihydroxyacetone, erthrulose, psicose, fructose, sorbose, or tagatose.

In one embodiment, $R^6$ is a monovalent radical of glucose, arabinose, or xylose, more typically, glucose.

When m=0, glycoside surfactant according to structure (II) is a monoglycoside surfactant. When m is greater than 0, the glycoside surfactant according to structure (II) is a polyglycoside surfactant.

In one embodiment, m is an integer greater than 0, —($R^5$)$_m$$R^6$ is a monovalent moiety consisting of a chain of m polymerized monomeric saccharide units $R^5$ with a terminal saccharide group $R^6$.

In one embodiment, each $R^5$ radical and the $R^6$ radical is a residue of the same saccharide compound. In one embodiment, each $R^5$ and $R^6$ is a glucose residue.

In one embodiment, each $R^5$ and $R^6$ group is independently selected from residues of different monosaccharides. In one embodiment, each $R^5$ and $R^6$ is independently selected from glucose residues, arabinose residues, and xylose residues, more typically, from arabinose residues and xylose residues.

In one embodiment, each $R^5$ and $R^6$ is independently selected from residues of a mixture of different monosaccharides and the glycoside surfactant according to formula (II) is a species according to formula (II-a):

$$R^4O-(R^{5'})_{m'}(R^{5''})_{m''}(R^{5'''})_{m'''}R^6 \quad\quad (II\text{-}a)$$

wherein:
  $R^4$, $R^5$, $R^6$, and m are each described as above,
  each $R^{5'}$, $R^{5''}$, and $R^{5'''}$ is an $R^5$ group, wherein $R^{5'} \neq R^{5''} \neq R^{5'''}$,
  each m', m", and m'" is an integer of from 0 to 10, wherein m'+m"+m'"=m, and
  the sequence of the $R^{5'}$, $R^{5''}$, and $R^{5'''}$ units in the —($R^{5'}$)$_{m'}$($R^{5''}$)$_{m''}$($R^{5'''}$)$_{m'''}$— chain is a random sequence or a block sequence, more typically, a random sequence.

In one embodiment, the glycoside surfactant is a mixture of monoglycosides, wherein the average value of m for the combined glycosides of the mixture is 1.

In one embodiment, the glycoside surfactant is a mixture of one or more monoglycoside and one or more polyglycoside, or a mixture of polyglucosides, wherein the average value of m for the combined glycosides of the mixture is greater than 1, typically greater than or equal to 1.1, more typically greater than or equal to 1.2 and even more typically greater than or equal to 1.3. In one embodiment, the average value of m is less than or equal to 8, more typically less than or equal to 4 and even more typically less than or equal to 2.

In one embodiment, the glycoside surfactant comprises one or more glycoside surfactants according to structure (II), wherein $R^4$ is alkyl, cycloalkyl, aryl, alkaryl, aralkyl, alkenyl, alkoxy, or aryloxy, more typically ($C_8$-$C_{22}$)alkyl, each $R^5$ and $R^6$ is independently a hexose residue, more typically a glucose residue, even more typically a D-glucose residue, and m is an integer of from 0 to 5, more typically 0 to 2.

In one embodiment, the glycoside surfactant comprises one or more glycoside surfactants according to structure (II), wherein: $R^4$ is alkyl, cycloalkyl, aryl, alkaryl, aralkyl, alkenyl, alkoxy, or aryloxy, more typically ($C_8$-$C_{22}$)alkyl, each $R^5$ and $R^6$ is independently a pentose residue, more typically arabinose residue or a xylose residue, even more typically, an L-arabinose residue or a D-xylose residue, and m is an integer of from 0 to 5, more typically 0 to 2.

Suitable glycoside surfactants include for example, (C$_4$-C$_{22}$)alkylhexosides, such as butylglucoside, octylglucoside, nonylglucoside, decylglucoside, undecylglucoside, dodecylglucoside, hexadecylglucoside, octadecylglucoside, erucylpolyglucoside, and mixtures thereof, (C$_4$-C$_{22}$)alkylpolyhexosides, such as butylpolyglucosides, octylpolyglucosides, nonylpolyglucosides, decylpolyglucosides, undecylpolyglucosides, dodecylpolyglucosides, tetradecylpolyglucosides, hexadecylpolyglucosides, octadecylpolyglucosides, erucylpolyglucosides, and mixtures thereof, (C$_4$-C$_{22}$)alkylpentosides, such as octylarabinoside, nonylarabinosides, decylarabinoside, dodecylarabinoside, hexadecylarabinoside, erucylarabinoside, octylxyloside, nonylxyloside, decylxyloside, dodecylxyloside, hexadecylxyloside, erucylxyloside and mixtures thereof, and (C$_4$-C$_{22}$)alkylpolypentosides, such as butylpolyarabinosides, octylpolyarabinosides, nonylpolyarabinosides, decylpolyarabinosides, undecylpolyarabinosides, dodecylpolyarabinosides, tetradecylpolyarabinosides, hexadecylpolyarabinosides, octadecylpolyarabinosides, erucylpolyarabinosides, butylpolyxylosides, octylpolyxylosides, nonylpolyxylosides, decylpolyxylosides, undecylpolyxylosides, dodecylpolyxylosides, tetradecylpolyxylosides, hexadecylpolyxylosides, octadecylpolyxylosides, and erucylpolyxylosides butylpoly(arabino-co-xylo)sides, octylpoly(arabino-co-xylo)sides, nonylpoly(arabino-co-xylo)sides, decylpoly(arabino-co-xylo)sides, undecylpoly(arabino-co-xylo)sides, dodecylpoly(arabino-co-xylo)sides, tetradecylpoly(arabino-co-xylo)sides, hexadecylpoly(arabino-co-xylo)sides, octadecylpoly(arabino-co-xylo)sides, erucylpoly(arabino-co-xylo)sides, and mixtures thereof, wherein the terminology "poly(arbino-co-xylo)side" denotes a copolymeric chain of monomeric residues of arabinose and xylose.

The adjuvant composition of the present invention is made by combining and mixing the respective ingredients together.

Suitable pesticides are biologically active compounds used to control agricultural pests and include, for example, herbicides, plant growth regulators, crop dessicants, fungicides, bacteriocides, bacteriostats, insecticides, and insect repellants, as well as their water soluble salts and esters. Suitable pesticides include, for example, triazine herbicides such as metribuzin, hexazinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glufosinate salts and esters and glyphosate salts and esters; dihalobenzonitrile herbicides such as bromoxynil, or ioxynil, benzoic acid herbicides such as dicamba, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chloronated aromatic fungicides such as chloroneb; dichloro aniline fungicides such as iprodione, strobilurin fungicides such as kresoxim-methyl, trifloxystrobin or azoxystrobin; chlorothalonil; copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoid insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources.

In one embodiment, the pesticide comprises one or more compounds selected from herbicides, plant growth regulators, crop dessicants, fungicides, bacteriocides, bacteriostats, insecticides, miticides, nematocides, insect repellants, and mixtures thereof.

In one embodiment, the pesticide is an herbicide or a mixture of herbicides, typically selected from glyphosate, glufosinate, dicamba, 2,4-D, their respective water soluble salts and esters, and mixtures thereof.

In one embodiment, the pesticide component of the pesticide composition of the present invention comprises a glyphosate herbicide selected from potassium salt of glyphosate, the sodium salt of glyphosate, the isopropyl amine salt of glyphosate, the ammonium salt of glyphosate, and mixtures thereof.

In one embodiment, the pesticide component of the pesticide composition of the present invention comprises a mixture of one or more water soluble salts or esters of glyphosate and one or more water soluble salts or esters of dicamba.

In one embodiment, the pesticide component of the pesticide composition of the present invention comprises a mixture of one or more water soluble salts or esters of glyphosate and one or more water soluble salts or esters of 2,4-D.

In one embodiment, the pesticide component of the pesticide composition of the present invention comprises a mixture of one or more water soluble salts or esters of glyphosate, one or more water soluble salts or esters of dicamba, and one or more water soluble salts or esters of 2,4-D.

In one embodiment, the pesticide component of the pesticide composition of the present invention comprises a mixture of one or more water soluble salts or esters of glufosinate, such as, for example, the ammonium salt of glufosinate, and one or more pesticide compounds selected from the water soluble salts or esters of glyphosate, the water soluble salts or esters of dicamba, and the water soluble salts or esters of 2,4-D.

Herbicidal compositions containing glyphosate or derivatives thereof are used to control a very wide variety of plants worldwide and can, when applied to the target plant in a herbicidally effective amount, reportedly control one or more target plant species of one or more of the following genera: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium,*

*Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea,* including annual broadleaf species such as, for example, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.), annual narrowleaf species such as for example, wild oat (*Avena fatua*), carpetgrass (*Axonopus* spp.), downy brome (*Bromus tectorum*), crabgrass (*Digitaria* spp.), barnyardgrass (*Echinochloa crusgalls*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*), perennial broadleaf species such as, for example, mugwort (*Artemisia* spp.), milkweed (*Asclepias* spp.), canada thistle (*Cirsium arvense*), field bindweed (*Convolvulus arvensis*) and kudzu (*Pueraria* spp.), perennial narrowleaf species such as for example, brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.), and other perennial species such as, for example, horsetail (*Equisetum* spp.), bracken (*Pteridium aquilinum*), blackberry (*Rubus* spp.) and gorse (*Ulex europaeus*).

The pesticide composition of the present invention is made by combining and mixing the respective ingredients together. In one embodiment, the pesticide composition is made by combining and mixing the adjuvant composition of the present invention, a pesticide compound, and water. Alternatively, the pesticide composition is made by combining and mixing the separate components of the adjuvant composition, a pesticide, and water.

In one embodiment, the adjuvant composition or, alternatively, the separate betaine surfactant and glycoside surfactant components, are combined with a pesticide, water and any optional ingredients and mixed to form a "spray mix" pesticide composition for application to target plants.

In one embodiment, the adjuvant composition or, alternatively, the separate betaine surfactant and glycoside surfactant components, are combined with a pesticide, water and any optional ingredients and mixed to form a pesticide concentrate composition, which is subsequently diluted with water, typically in a ratio of from 1:10 to 1:100 parts by weight pesticide concentrate composition: parts by weight water to form a spray mix pesticide composition for applying to target plants.

In one embodiment, the pesticide composition is a pesticide concentrate that comprises, based on 100 pbw of the adjuvant composition:
(a) a combined amount of from about 0.1 to about 20 pbw, more typically from about 0.1 to about 10 pbw, and still more typically from about 0.5 to about 8 pbw of one or more betaine surfactants and one or more glycoside surfactants, wherein the combined amount of the one or more betaine surfactants and one or more glycoside surfactants, comprises, based on 100 parts by weight of the combined amount:
  (i) from about 50 to less than 100 parts by weight of the one or more betaine surfactants, and
  (ii) from greater than 0 to about 50 parts by weight of one or more glycoside surfactants,
(b) from about 30 to about 60 pbw more typically from about 35 to about 55 pbw of a pesticide, and
(c) from about 30 to about 69.9 pbw, more typically, from about 37 to about 64.5 pbw water.

In one embodiment, the pesticide composition is a spray mix that comprises, based on 100 pbw of the spray mix composition:
(a) from about 0.001 to about 1 pbw, more typically from about 0.005 to about 0.88 pbw, of a combined amount of one or more betaine surfactants and the one or more glycoside surfactants, wherein the combined amount of the one or more betaine surfactants and one or more glycoside surfactants, comprises, based on 100 parts by weight of the combined amount:
  (i) from about 50 to less than 100 parts by weight of the one or more betaine surfactants, and
  (ii) from greater than 0 to about 50 parts by weight of one or more glycoside surfactants
(b) from about 0.3 to about 6 pbw more typically from about 0.35 to about 5.5 pbw of a pesticide, and
(c) from about 93 to about 99 699 pbw, more typically from about 93.62 to about 99.645 pbw water.

In one embodiment of the pesticide composition of the present invention, the combined amount of the one or more glycoside surfactants and the one or more betaine surfactants comprises, based on 100 pbw of the combined amount:
(i) from about 60, more typically about 65 pbw, even more typically about 70 pbw, and still more typically about 75 pbw, to less than 100 pbw, more typically about 99 pbw, even more typically about 98 pbw, and still more typically about 97 pbw, of the one or more betaine surfactants, and
(i) from greater than 0, more typically about 1 pbw, even more typically about 2 pbw, and still more typically about 3 pbw, to about 40 pbw, more typically about 35 pbw, even more typically about 30 pbw, and still more typically about 25 pbw, of the one or more glycoside surfactants.

In one embodiment of the pesticide composition of the present invention, the combined amount of the one or more glycoside surfactants and the one or more betaine surfactants comprises, based on 100 pbw of the combined amount:
(i) from about 60 to less than 100 pbw, more typically from about 65 to about 99 pbw, even more typically from about 70 to about 98 pbw, and still more typically from about 75 to about 97 pbw, of the one or more betaine surfactants, and
(i) from greater than 0 to about 40 pbw, more typically from about 1 to about 35 pbw, even more typically from about 2 to about 30 pbw, and still more typically from about 3 to about 25 pbw, of the one or more glycoside surfactants.

In one embodiment, the pesticide composition comprises a herbicidally effective amount of a pesticide, more typically, the pesticide is glyphosate herbicide and the pesticide composition is an herbicide composition that comprises a herbicidally effective amount of glyphosate.

In one embodiment, the pesticide composition is a pesticide concentrate that comprises, based on 100 pbw of the composition, from about 1 pbw to about 90 pbw, more typically from about 10 to about 80 pbw, and even more typically from about 30 to about 60 pbw, of the pesticide, more typically of a glyphosate herbicide.

The adjuvant and pesticide compositions of the present invention may each, optionally, further comprise one or more agronomically acceptable solvent or carrier in addition to water. Suitable solvents include water miscible organic solvents, such as alcohols, more typically ($C_1$-$C_8$)alcohols, such as ethanol, glycols, such as ethylene glycol, and polyglycols, such as polyethylene glycol, and N-alkyl pyrrolidones, as well as water immiscible organic solvents, such as, for example, alkylated aromatic solvents, such as toluene or alkylated naphthalenes and mineral oil fractions, such as paraffinic hydrocarbons.

In one embodiment, the adjuvant composition of the present invention further comprises, based on 100 pbw of such composition, up to about 25 pbw a water miscible organic solvent, a water immiscible organic solvent, or a mixture thereof.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example 0-0-1 3%-S; 3%-Zn; 2%-Fe; 2%-Mn and mixtures thereof. In one embodiment, the pesticide composition comprises from about 85 to about 99 pbw, more typically from about 90 to about 99 pbw, and even more typically from about 93 to about 99 pbw, of a mixture of fertilizer and water.

In one embodiment, the pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

The pesticide composition of the present invention may, optionally, further comprise other ingredients, such as one or more additional surfactants, one or more thickeners, such as polysaccharide thickeners, and polyacrylamide thickeners, as well as antifoams, spreaders, and drift control agents.

The adjuvant composition may optionally further comprise other surfactants in addition to the one or more glycoside surfactants and the one or more betaine surfactants. Such additional surfactants may be selected from anionic surfactants, cationic surfactants, nonionic surfactants, amphoteric surfactants and zwitterionic surfactants.

In one embodiment, the pesticide composition of the present invention is applied to foliage of a target plant at a rate of from about 0.25 pint, more typically about 0.5 pint, to about 5 pints, even more typically from about 1 pint to about 4 pints, as expressed in terms of the above described pesticide concentrate embodiment of the pesticide composition of the present invention (that is, comprising, based on 100 pbw of such composition, from about 30 to about 60 pbw, more typically from about 35 to about 55 pbw of a pesticide) per acre.

In one embodiment, the pesticide composition is spray applied via conventional spray apparatus to foliage of one or more target plants present on an area of ground at a rate of from about 1 gallon to about 20 gallons, more typically about 3 gallons to 20 gallons, of the above described spray mix embodiment of the pesticide composition per acre of ground.

EXAMPLES 1-3 AND COMPARATIVE EXAMPLES C1-C3

The pesticide compositions of Examples 1-3 and Comparative Examples $C_1$-$C_3$ were aqueous solutions made by combining the ingredients in the relative amounts (based on 100 pbw of the respective pesticide composition) set forth in Tables I and II below and mixing:

TABLE I

| Ex # | glyphosate IPA (pbw) | ($C_{12}$-$C_{14}$)alkyl dimethylbetaine (pbw) | ($C_8$-$C_{10}$)alkyl polyglucoside (pbw) | water (pbw) |
|---|---|---|---|---|
| 1 | 41.8 | 2.93 | 0.36 | 54.91 |
| 2 | 41.8 | 2.79 | 0.72 | 54.69 |
| 3 | 41.8 | 1.86 | 2.9 | 53.44 |
| C1 | 41.8 | 3.1 | 0 | 55.1 |
| C2 | 41.8 | 0 | 7.24 | 50.96 |
| C3 | 41.8 | 0 | 0 | 58.2 |

The efficacy of the compositions in controlling plant growth was tested, in 3 replicates, by diluting each of the compositions of Examples 1-3 and C1-C3 1:88 with water and applying each of the dilute pesticide compositions at a rate of 10 gallons per acre (0.25 pint glyphosate, as acid equivalent, per acre using a stationary track sprayer to each of the plant species listed below.

| | |
|---|---|
| Corn | "CN" |
| Shattercane | "SC" |
| Barnyard grass | "BG" |
| Velvetleaf | "VL" |
| Hemp Sesbania | "HS" |
| Ivyleaf Morning Glory | "IM" |
| Soybean | "SB" |
| Kochia | "KO" |
| Sicklepod | "SP" |
| Lambsquarter | "LQ" |
| Purslane | "PS |

Results at 28 days post application are given in Parts A and B of TABLE II below as percent control of plant growth, as indicated by plant weight, for each of the various plant species tested, averaged in each case for the 3 replicates, and as an overall average value for all species tested ("Ave.").

TABLE III

Part A

% Control of Plant Growth

| Ex # | CN | SH | BN | VL | HS | IM |
|---|---|---|---|---|---|---|
| 1 | 70 | 90 | 60 | 50 | 50 | 70 |
| 2 | 60 | 70 | 50 | 40 | 40 | 50 |
| 3 | 60 | 60 | 0 | 40 | 40 | 40 |
| C1 | 40 | 60 | 40 | 20 | 20 | 20 |
| C2 | 60 | 60 | 20 | 10 | 0 | 0 |
| C3 | 70 | 60 | 0 | 40 | 0 | 0 |

TABLE II

Part B

| | | % Control of Plant Growth | | | | |
|---|---|---|---|---|---|---|
| Ex # | SB | KO | SP | LQ | PS | Ave. |
| 1 | 0 | 60 | 50 | 60 | 60 | 56 |
| 2 | 0 | 40 | 30 | 80 | 60 | 47 |
| 3 | 0 | 40 | 0 | 60 | 60 | 36 |
| C1 | 0 | 0 | 2 | 40 | 0 | 24 |
| C2 | 0 | 60 | 0 | 80 | 60 | 32 |
| C3 | 0 | 0 | 0 | 10 | 20 | 18 |

The invention claimed is:

1. A pesticide composition, comprising, based on 100 parts by weight of the composition:
   (a) from greater than 0 to about 20 parts by weight of a combined amount of one or more betaine surfactants, and one or more glycoside surfactants, comprising, based on 100 parts by weight of the combined amount:
      (i) from about 50 to less than 100 parts by weight of the one or more betaine surfactants,
         said betaine surfactant comprising one or more compounds according to formula (I):

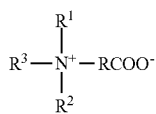

(I)

wherein:
R is methylene or dimethylene,
$R^1$ and $R^2$ are each independently alkyl, alkenyl, alkoxyalkyl, hydroxyalkyl, hydroxy-terminated poly(oxyalkylene), or alkoxy-terminated poly(oxyalkylene), and
$R^3$ is a $(C_6$-$C_{30})$alkyl,
and
      (ii) from greater than 0 to about 50 parts by weight of one or more glycoside surfactants,
         said glycoside surfactant comprising one or more compounds according to formula (II):

$$R^4O(R^5)_mR^6 \quad (II)$$

wherein:
$R^4$ is a $(C_8$-$C_{22})$alkyl,
each $R^5$ is independently a divalent monosaccharide radical,
$R^6$ is a monovalent monosaccharide radical, and
m is an integer of from 0 to about 10,
(b) water, and
(c) one or more pesticides selected from glyphosate, glufosinate, dicamba, 2,4-D, their respective water soluble salts and esters, and mixtures thereof.

2. The composition of claim 1, wherein the combined amount of the one or more betaine surfactants and one or more glycoside surfactants, comprises, based on 100 parts by weight of the combined amount:
   (i) from about 75 to less than 100 parts by weight of the one or more betaine surfactants, and
   (i) from greater than 0 to about 25 parts by weight, of the one or more glycoside surfactants.

3. The composition of claim 1, wherein:
the betaine surfactant comprises one or more compounds according to formula (I):

(I)

wherein:
R is methylene,
$R^1$ and $R^2$ are each independently $(C_1$-$C_6)$alkyl, and
$R^3$ is $(C_6$-$C_{30})$alkyl, and
the glycoside surfactant comprises one or more compounds according to formula (II):

$$R^4O(R^5)_mR^6 \quad (II)$$

wherein:
$R^4$ is $(C_8$-$C_{22})$alkyl,
each $R^5$ and $R^6$ is a glucose residue, and
m is an integer of from 0 to 5.

4. The composition of claim 1, wherein the pesticide comprises a glyphosate herbicide selected from potassium salt of glyphosate, the sodium salt of glyphosate, the isopropyl amine salt of glyphosate, the ammonium salt of glyphosate, and mixtures thereof.

5. A pesticide composition, comprising, based on 100 parts by weight of the composition:
   (a) from greater than 0 to about 20 parts by weight of a combined amount of one or more betaine surfactants, and one or more glycoside surfactants, comprising, based on 100 parts by weight of the combined amount:
      (i) from about 75 to less than 100 parts by weight parts by weight of $(C_{12}$-$C_{14})$alkyl dimethylbetaine surfactants, and
      (ii) from greater than 0 to about 25 parts by weight of $(C_8$-$C_{10})$alkyl polyglucoside surfactants,
   (b) water, and
   (c) one or more pesticides, comprising the isopropyl amine salt of glyphosate.

* * * * *